(12) United States Patent
Murie et al.

(10) Patent No.: US 6,454,888 B1
(45) Date of Patent: Sep. 24, 2002

(54) METHODS OF CHANGING SIZE OF PANT-TYPE PERSONAL CARE ARTICLES OUTPUTTED FROM A MANUFACTURING PROCESS

(76) Inventors: Denise Marie Bell Murie, 1109 Pendleton Rd., Neenah, WI (US) 54956; Keith Joseph Renard, 4358 Breezewood La., Oshkosh, WI (US) 54904; Daniel Mark Duhm, N1235 Bobwhite Dr., Greenville, WI (US) 54952; Russell Evan Thorson, 2004 W. Seneca Dr., Appleton, WI (US) 54914

( * ) Notice: Subject to any disclaimer, the term of this patent is extended or adjusted under 35 U.S.C. 154(b) by 0 days.

(21) Appl. No.: 09/834,787

(22) Filed: Apr. 13, 2001

(51) Int. Cl.$^7$ ............................................... B32B 31/00
(52) U.S. Cl. .......................... 156/64; 156/360; 156/361
(58) Field of Search .......................... 156/64, 66, 73.1, 156/360, 361, 196, 363, 227, 250, 256, 264, 269

(56) References Cited

U.S. PATENT DOCUMENTS

| | | | |
|---|---|---|---|
| 5,690,627 A | 11/1997 | Clear et al. ............... | 604/385.2 |
| 5,846,232 A | 12/1998 | Serbiak et al. ............ | 604/385.2 |
| 5,930,139 A | * 7/1999 | Chapdelaine et al. .. | 364/468.25 |
| 6,022,432 A | 2/2000 | Elsberg et al. ............. | 156/73.1 |
| 6,036,805 A | 3/2000 | McNichols .................. | 156/227 |
| 6,077,379 A | * 6/2000 | Herrin et al. ............... | 156/269 |
| 6,113,717 A | 9/2000 | Vogt et al. .................. | 156/73.1 |
| 6,277,223 B1 | * 8/2001 | Herrin et al. .............. | 156/73.1 |

* cited by examiner

Primary Examiner—Mark A. Osele
Assistant Examiner—George R. Koch, III
(74) Attorney, Agent, or Firm—Wilhelm Law Service; Thomas D. Wilhelm

(57) ABSTRACT

Methods of changing from manufacture of pant-type refastenable personal care articles of a first size to manufacture of such pant-type refastenable personal care articles of a second different size. A method of the invention comprises defining in the workpiece, at at least one side edge of the respective workpiece, a length of material defined in the machine direction, wherein activity, or inactivity, of such length of material, in combination with other elements of the workpiece, determines the size of the pant-type refastenable personal care article being so produced, whereby the length of material so defined can be activated and thereby incorporated into the personal care article to correspondingly produce a relatively larger size such personal care article, or inactivated and thereby excluded from the personal care article to correspondingly produce a relatively smaller size personal care article.

19 Claims, 4 Drawing Sheets

METHODS OF CHANGING SIZE OF PANT-TYPE PERSONAL CARE ARTICLES OUTPUTTED FROM A MANUFACTURING PROCESS

BACKGROUND OF THE INVENTION

This invention relates to methods for changing sizes of pant-type personal care articles outputted from a manufacturing process. More specifically, this invention relates to methods for changing sizes in especially the circumferential waist components of pant-type refastenable personal care articles. The methods of the invention attenuate the counterproductive aspects of down time on manufacturing lines to change and adjust function rolls and other components necessary for changing production from first articles having a first waist size to second different articles having a second different waist size, of pant-type, especially refastenable, absorbent personal care articles.

In conventional methods for fabricating disposable pant-type personal care articles of differing sizes, it is known to stop manufacturing line production of personal care articles of a first size to one or both replace and reposition function rolls and adjust timing of manufacturing line components to produce personal care articles of a second different size on the same manufacturing line. The down time associated with a conventional such production change-over is typically significant. The main reason for such significant down time is related to conventional methods of changing the product length, also known as repeat length, in order to effect change in product (e.g. waist) size.

In such conventional size change-over, function rolls are typically either exchanged, or moved in the machine direction along the manufacturing line, to accommodate changes in lengths of, for example, front portions and back portions of such personal care articles, defining first and second different waist sizes thereby to define respective first and second sizes of such pant-type personal care articles. Similarly, other manufacturing components are typically adapted to such size changes while the manufacturing process is stopped. For example, knife repeat distances may be adjusted, or a knife or knives may be moved, to compensate for changed cutting requirements. Timing of front fastener panel application and/or hook tab fastener application may also need to be adjusted in the machine direction to compensate for waist size differentiation between different sizes of personal care articles. In sum, the conventional method of making a size change is to shut down the production line and, while production is shut down, to physically adjust or move selected machines and/or other mechanical devices in order to effect the change to making a second different size of personal care article.

A need exists for improved methods for production of pant-type personal care articles wherein the methods are effective to attenuate down time for effecting size changes on a manufacturing line as well as to reduce cost to manufacturers by enabling manufacturers to use manufacturing line components in common to produce pant-type personal care articles in both first and second sizes.

Thus, it is an object of this invention to provide methods for production of pant-type personal care articles in both first and second sizes on a manufacturing line while attenuating down time.

It is a further object to provide manufacturing processes which reduce cost to manufacturers by enabling a manufacturer to use the same manufacturing line components in producing first and second sizes of pant-type personal care articles.

It is another object to provide a manufacturing process wherein the manufacturing process can be changed to produce a second different size pant-type personal care article without shutting down the manufacturing process for a significant duration of time.

It is yet another object to provide methods wherein workpieces, including a defined length of material, have a common dimension, leading edge-to-leading edge, in the machine direction of the manufacturing process both with inclusion of the length of material and with exclusion of the length of material.

SUMMARY OF THE DISCLOSURE

In a first family of embodiments, the invention comprehends a method of changing from manufacture of pant-type refastenable personal care articles of a first size to manufacture of such pant-type refastenable personal care articles of a second different size. The method takes place in a process for manufacturing pant-type refastenable personal care articles in a format which includes defining a stream of workpieces connected to each other along a web having an indefinite length. A respective such personal care article has a front portion, a rear portion, and a crotch portion. The method comprises, with respect to each workpiece, defining in the web or workpiece a length of material defined in the machine direction wherein activity of such length of material, in combination with other elements of the web or workpiece, determines the size of the pant-type refastenable personal care article being so produced, whereby the length of material can be activated to thereby produce relatively larger such personal care articles, or inactivated to produce relatively smaller such personal care articles. The method also comprises changing activity of the lengths of material so defined, thereby to affect size change in the respective personal care articles being produced while maintaining the so-defined lengths of material in the web at least until the respective workpieces are separated from the web.

In some embodiments, the method includes such workpieces, including the defined length of material, having a common dimension, leading edge-to-leading edge, in the machine direction of such manufacturing process both with inclusion of the length of material and with exclusion of the length of material.

In preferred embodiments, first and second side seam bonds are formed on opposing sides of respective ones of adjoining workpieces, and inboard edges of adjacent side seam bonds on adjacent workpieces are spaced from each other by a first distance. In such embodiments, the method further includes changing the activity of the length of material by manufacturing workplaces having the inboard edges of adjacent such side seam bonds spaced from each other by a second distance different from the first distance.

The invention can include inactivating the length of material by manufacturing workpieces having the inboard edges of adjacent such side seam bonds spaced from each other by a second distance greater than the first distance.

In some embodiments, the method includes changing timing and thus location of forming of side seam bonds on the respective workpieces, in combination with timing and thus location of formation of cuts separating such workpieces from the web, thereby effecting a size change in the personal care articles being so produced, sufficient in magnitude to be discernable in routine consumer sales.

In other embodiments, the method includes changing one or both timing and loci of side seam bonder apparatus components, and thus location of formation of side seam bonds on the respective workpieces, in combination with changing one or both timing and loci of separation apparatus components, and thus location of formation of cuts separating such workpieces from the web while continuing ongoing production of such personal care articles.

In a second family of embodiments, the invention comprehends the length of material so defined being activated and thereby incorporated into the personal care article to correspondingly produce a relatively larger such personal care article, or inactivated and thereby excluded from the personal care article to correspondingly produce a relatively smaller personal care article.

In preferred embodiments, the method includes defining first and second such lengths of material at opposing first and second such side edges of the respective workpiece, and controlling activity of such lengths of material thereby to determine the size of the respective pant-type refastenable personal care article.

In some embodiments, the method includes changing one or both timing and loci of side seam bonder apparatus components, and thus location of forming of side seam bonds on the respective workpieces from the web, and thereby effecting a size change in the personal care articles being so produced, sufficient in magnitude to be discernable in routine consumer distribution.

In a third family of embodiments, the invention comprehends a method wherein each workpiece has bonds joining the front portion and the rear portion to each other at the side edges, and each such bond has an inwardly-disposed edge disposed away from the respective side edge of such workpiece. The method comprises with respect to each workpiece, defining in the web or workpiece, at the side edges of the respective workpiece, a length of material defined in the machine direction, wherein incorporation of such length of material, in combination with other elements of the web or workpiece, inwardly of the inwardly-disposed edges, produces a pant-type refastenable personal care article of a relatively larger size, and wherein exclusion of such length of material from the workplace produces a pant-type refastenable personal care article of a relatively smaller size; and changing use of the lengths of material so defined, from inclusion to exclusion or from exclusion to inclusion, thereby to effect size change in the respective personal care articles being produced while maintaining the so-defined lengths of material in the web at least until the respective workpieces are separated from the web.

In a fourth family of embodiments, the invention comprehends a method including initiating such manufacturing process and thereby beginning manufacture of an ongoing stream of such personal care articles. The method includes, while continuing to manufacture the ongoing stream of such personal care articles, changing activity of part or all of ones of the lengths of material so defined, thereby to effect a size change in the respective personal care articles being produced.

The method can include separating successive ones of the workpieces from the web, and separating the inactivated lengths of material from both of the adjacent respective workpieces.

In some embodiments, the method includes employing a programmable logic computer to instruct bonding apparatus regarding one or both proper timing and positioning of bonder components, and thus location for forming the side seam bonds. The method can also include employing a programmable logic computer to instruct separation apparatus regarding one or both proper timing and positioning of separator components, and thus location on the workpieces for separation of the respective workpieces from the web, and from the inactivated lengths of material.

Figure 1A:
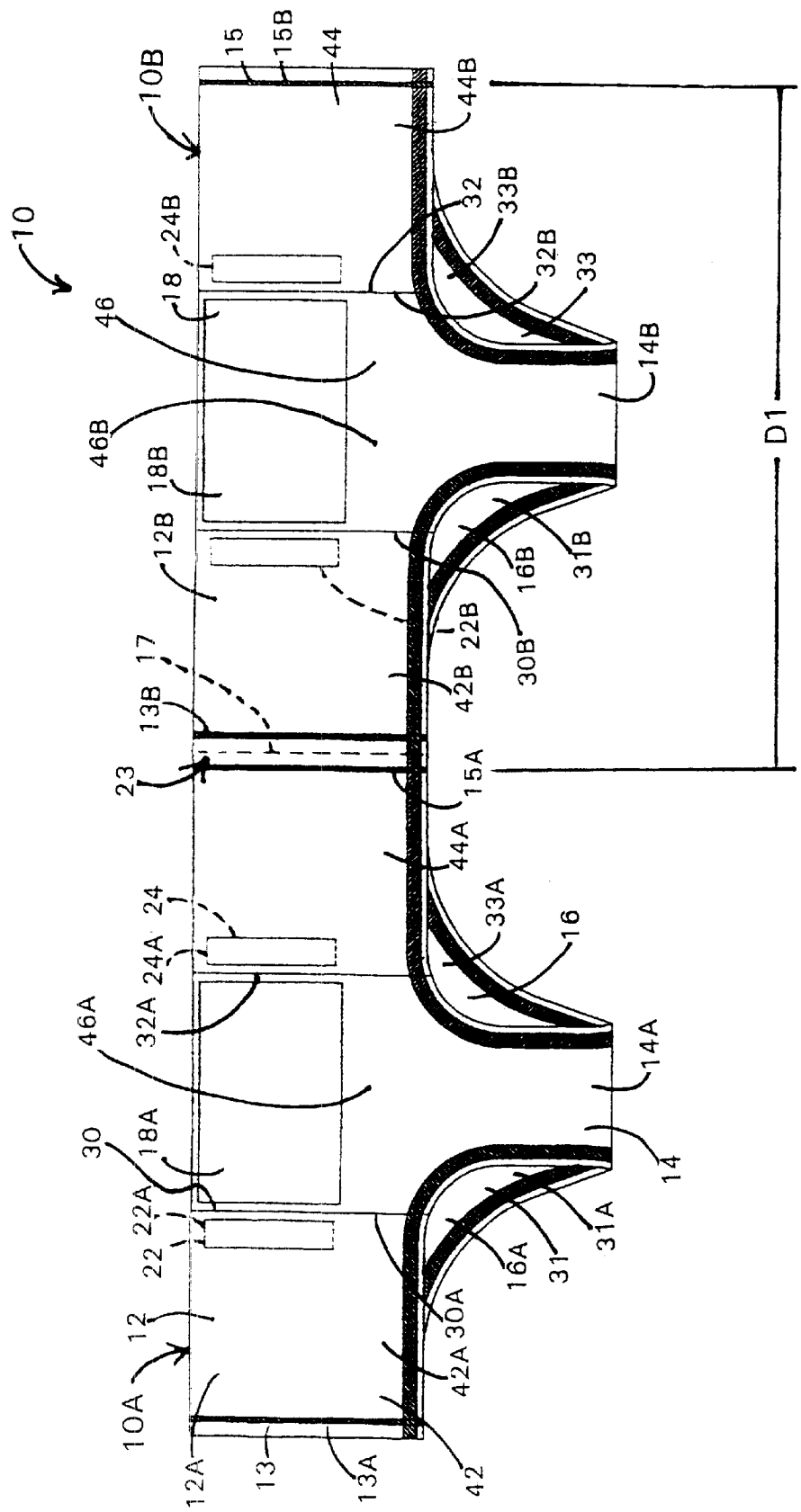
FIG. 1A shows a plan view of first and second personal care articles which can be made employing methods of the invention and demonstrating a first size.

The invention is not limited in its application to the details of the construction and the arrangement of the components set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

This invention relates to pant-type refastenable personal care article manufacturing processes and products so produced. Methods of the invention effect a transition from manufacturing personal care articles of a larger waist size to manufacturing personal care articles of a smaller waist size by decreasing the distance between the opposing side seam bonds on the personal care articles being produced, whereby waist circumference is reduced. Correspondingly, the distance between adjacent workpieces is increased.

In contrast, methods of the invention effect the opposite transition, from manufacturing personal care articles of a smaller waist size to manufacturing personal care articles of a larger waist size by increasing the distance between the opposing side seam bonds on the personal care articles being produced, whereby waist circumference is enlarged. Correspondingly, the distance between the inwardly-disposed edges of side seam bonds of adjacent workpieces is decreased.

Figure 3:
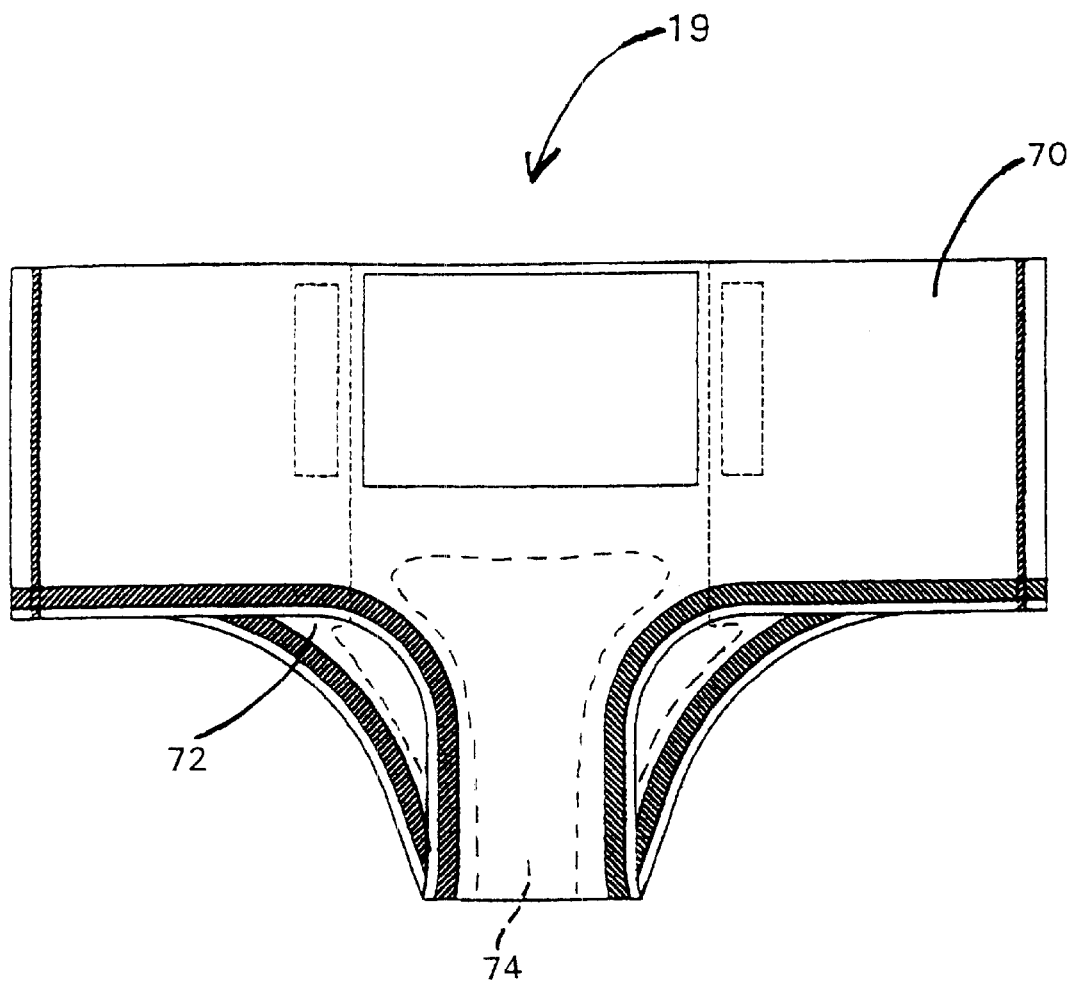
FIG. 3 shows a plan view of a personal care article of the invention, illustrating representative component layers of such personal care articles.

Referring to FIG. 3, a personal care article 19 of the invention generally comprises an outer liquid-impermeable cover 70, a liquid-permeable bodyside liner 72, and an absorbent core 74 disposed between outer cover 70 and bodyside liner 72.

Various woven and nonwoven fabrics can be used for bodyside liner 72. For example, bodyside liner 72 can be e.g. a meltblown or spunbonded or other non-woven web of polymeric material selected from the group consisting of polyolefins including polyethylenes and polypropylenes, polyesters, and polyamides, and mixtures, copolymers, and blends of such polymeric fibers. Bodyside liner 72 may also comprise a carded and/or bonded web composed of natural and/or synthetic fibers. The bodyside liner can be composed of a substantially hydrophobic material wherein the hydrophobic material is treated with a surfactant or otherwise processed to impart a desired level of wetability and hydrophilicity.

Bodyside liner 72 can comprise nonwoven, spunbonded, polypropylene fabric fabricated with 2.8–3.2 denier fibers, formed into a web having a basis weight of e.g. about 22 grams per square meter and a density of e.g. about 0.06 grams per cubic centimeter. The fabric is preferably surface treated with e.g. about 0.3 weight percent of a surfactant. Bodyside liner 72 typically comprises a fibrous web defining a multiplicity of small e.g. microporous openings randomly spaced between the fibers and according to location and orientation of the fibers, extending from a major surface of the web into the interior of the web. Such small openings typically extend through the entirety of the thickness of the web.

Addressing structure, bodyside liner 72 can be fabricated using material selected from the group consisting of porous foams, reticulated foams, apertured polymeric films, polymeric fibers, and natural fibers. Bodyside liner 72 can comprise a multiplicity of components or layers which correspond to any of the materials disclosed herein, as well as others known in the art.

It is generally preferred that outer cover 70 of the personal care article be formed from a material which is substantially impermeable to aqueous liquids. A typical outer cover 70 can be manufactured from a thin plastic film or other flexible liquid-impermeable material. For example, outer cover 70 can be formed from a film of polymeric material selected from the group consisting of polyolefins including polyethylenes and polypropylenes, polyesters, and polyamides, and mixtures, copolymers, and blends of such polymeric materials, having thicknesses, for example, of from about 0.012 millimeter to about 0.13 millimeter.

In embodiments where outer cover 70 should have a more cloth-like feel, the outer cover can comprise a polyethylene film having a nonwoven web, such as a spunbonded web of polyolefin fibers, bonded to a surface thereof. For example, a polyethylene film having a thickness of about 0.015 millimeter can have thermally or otherwise bonded thereto a spunbonded web of polyolefin fibers having fiber thicknesses of from about 1.5 to about 2.5 denier per filament, which spunbonded web has a basis weight of e.g. about 24 grams per square meter.

Further, outer cover 70 can be formed of a woven or nonwoven fibrous web which has been totally or partially constructed or treated to impart a desired level of aqueous liquid impermeability to selected regions which are e.g. adjacent or proximate absorbent core 74.

Still further, outer cover 70 can optionally be composed of a micro-porous material which permits vapors to escape from absorbent core 74 and through outer cover 70 while preventing liquid exudates from passing through the outer cover.

One or both of outer cover 70 and bodyside liner 72 can comprise a fibrous web defining a multiplicity of randomly-spaced small openings extending from a major surface of the web into the interior of the web. Polymeric material such as the recited polyolefins including polyethylenes and polypropylenes, polyesters, and polyamides, and mixtures, copolymers, and blends of such polymeric materials can be used in either film form or in non-woven fiber form, for one or both of bodyside liner 72 and outer cover 70. As to bodyside liner 72, films are apertured films. As to outer cover 70, fibrous webs are impermeable to e.g. aqueous liquid.

Included in the definition of polymeric material above are all routine, common, normal additives known to those skilled in the art of polymeric materials such as processing aids, chemical stabilizers, compatibilizers e.g. where more than one polymer or other material is used, fillers, and the like.

Absorbent core 74 suitably comprises hydrophilic fibers, such as a web or matt or loose collection of cellulosic fluff, in combination with a high-absorbency material commonly known as superabsorbent material. Absorbent core 74 preferably comprises a mixture of superabsorbent hydrogel-forming particles and wood pulp fluff. In place of the wood pulp fluff, one can use synthetic, polymeric, meltblown fibers or a combination of meltblown fibers and natural fibers. The superabsorbent material can be substantially homogeneously mixed with the hydrophilic fibers or can be otherwise combined into absorbent core 74.

Alternatively, absorbent core 74 can comprise a laminate of fibrous webs and superabsorbent material or other suitable means of maintaining a superabsorbent material in a localized area. Absorbent core 74 can additionally comprise an un-creped through air dried paper web material known as UCTAD.

Absorbent core 74 can have any of a number of shapes. For example and without limitation, absorbent core 74 can be rectangular, I-shaped or T-shaped. In such products as e.g. refastenable absorbent articles, pants, and the like, absorbent core 74 is preferably narrower in the crotch portion than in the rear portion or the front portion, especially where the crotch portion of the absorbent article is narrower than the rear portion or the front portion.

The high-absorbency material in absorbent core 74 can be selected from natural, synthetic and modified natural polymers and materials. The high absorbency material can be inorganic material, such as silica gels, or organic compounds, such as cross-linked polymers. The high absorbency material refers to any structure or composition, along with associated process, which renders normally water-soluble material substantially water insoluble but swellable, whereby absorbent properties are available but the swelled material is substantially immobile after absorbing water-based liquid. Such superabsorbent material can be fabricated by creating e.g. physical entanglement, crystalline domains, covalent bonds, ionic complexes and associations, hydrophilic associations such as hydrogen bonding, and hydrophobic associations, or Van der Waals forces. Two such superabsorbents are DRYTECH® 2035 M and FAVOR® SXM 880. DRYTECH® availiabe from the Dow Chemical Company. Midland, Michigan. FAVOR® is available from Stockhausen, Inc., Greensboro, N.C.

Figure 1B:
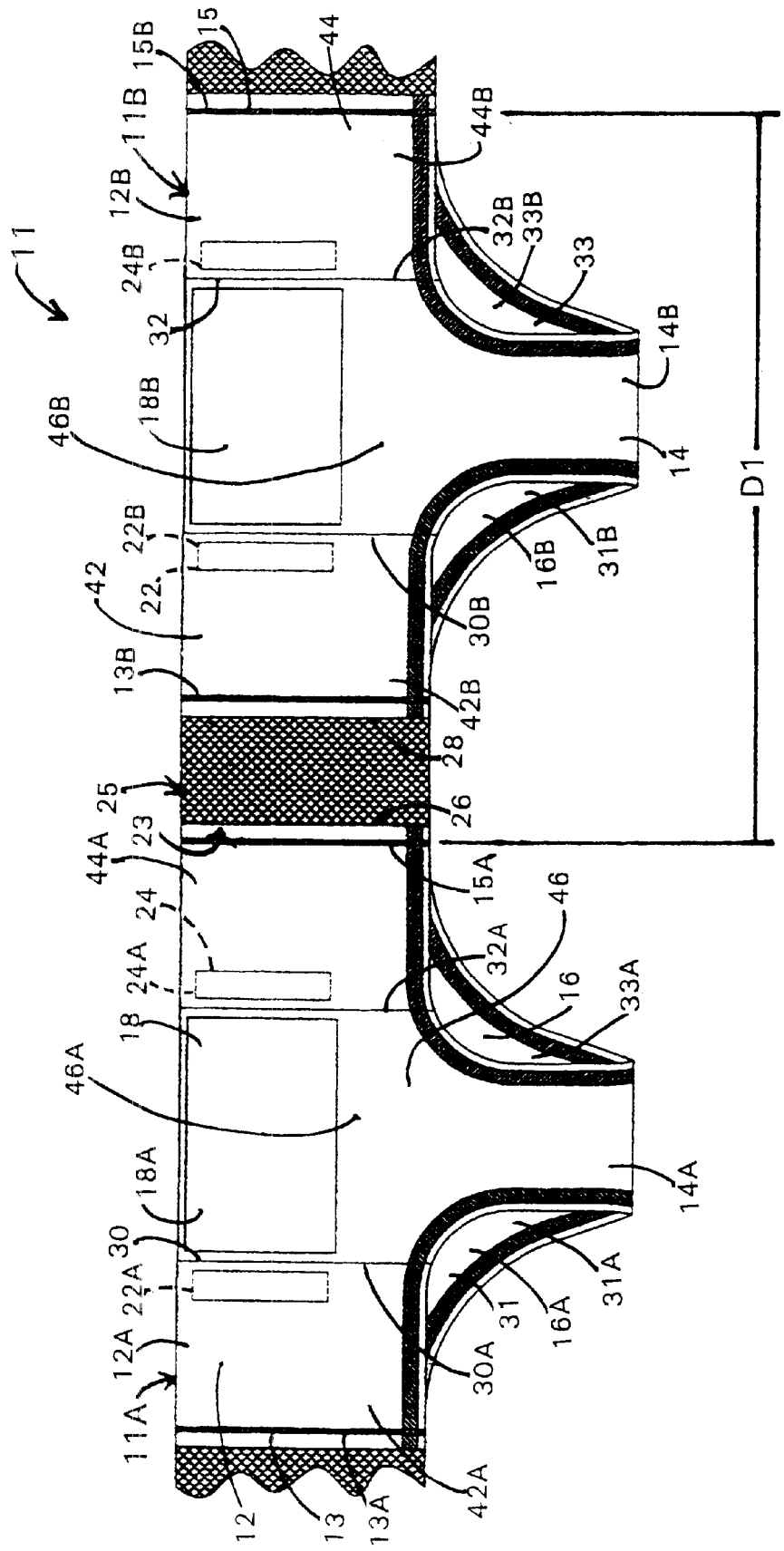
FIG. 1B shows a plan view of first and second personal care articles which can be made employing methods of the invention and demonstrating a second size in combination with the same respective length, leading edge-to-leading edge, as in the personal care article of FIG. 1A.

FIG. 1A illustrates a first refastenable pant-type personal care article 10A and a second refastenable pant-type personal care article 10B, collectively articles 10, attached to each other in e.g. web form prior to separation of the respective articles from each other e.g. on a manufacturing line. Both articles 10A and 10B reflect potential for a first refastened size. Similarly, FIG. 1B shows a first refastenable pant-type personal care article 11A and a second refastenable pant-type personal care article 11B, collectively articles 11, both reflecting potential for a second refastened size. Personal care articles 11 of FIG. 18 represent a potentially relatively smaller size personal care article than personal care articles 10 of FIG. 1A. In both FIGS. 1A and 1B, first and second ones of the personal care articles are illustrated employing "A" and "B" suffixes to represent elements of the respective first and second personal care articles.

Referring to personal care articles 10 of FIG. 1A and personal care articles 11 of FIG. 1B, each personal care article comprises a front portion 12, a rear portion 16, and a crotch portion 14 located between front portion 12 and rear portion 16. First side seam 13 and second side seam 15 of each respective personal care article adhere front portion 12 to rear portion 16 of each respective personal care article at the side seam location.

A cut zone 23 is located between each pair of side seams 13, 15 associated with adjacent ones of the personal care articles on the manufacturing line. When fabrication of a given personal care article workpiece, in the web of personal care article workpieces being fabricated, has been completed in web form, the respective personal care article workpiece is separated from the web by e.g. severing the workpiece in cut zone 23. For relatively larger personal care articles 10 of a first size in FIG. 1A, each personal care article is separated from the web by severing the workpiece at a cut line represented by dashed line 17, positioned in cut zone 23. Dashed line 17 can also represent a line of perforations rather than a cut line, whereupon separation of the workpieces from each other is accomplished by tearing the workpieces from each other at the line of perforations.

For relatively smaller personal care articles 11 of the second smaller size illustrated in FIG. 1B, each personal care article is separated from the web by separating the workpiece at or adjacent first and second edges 26, 28 of excision section 25, positioned in cut zone 23. Each personal care article is preferably separated from the web to create the stand-alone resultant personal care article, ready for e.g. packaging or other suitable treatment. As in the article embodiment illustrated in FIG. 1B, excision section 25 can be removed by making cuts at both edges 26 and 28. In the alternative, excision section 25 can be removed by making lines of perforations at edges 26, 28, in combination with tearing of the material at the lines of perforations, at desired times.

Fastener-receptive area 18 is disposed at a central region of front portion 12 of the outer cover of the personal care article. While fastener-receptive area 18 is displayed as being a one-component, generally rectangular-shaped piece of landing zone material, the fastener-receptive area can comprise a variety of shapes and sizes, and any desired number of separate components. Further, in some embodiments, some or all of the outer cover can comprise suitable landing zone material such that landing zone properties are integral with the outer cover.

Therefore, a fastener-receptive area may or may not have distinct physical edges, depending on- whether the fastening properties desired to be performed thereby (i) are provided by distinct separate e.g. landing zone component(s) or (ii) are integral with a surface of front portion 12.

Referring to personal care article 10A, first fastener 22A is disposed between fastener-receptive area 18A and first side seam 13A, and similarly, second fastener 24A is disposed between fastener-receptive area 18A and second side seam 15A. Between fastener-receptive area 18A and first fastener 22A is located a first line of weakness 30A. Similarly, a second line of weakness 32A is disposed between the landing zone and second fastener 24A.

Fasteners 22A, 24A, as illustrated herein, define attachment structures which, e.g. in combination with fastener-receptive area 18A, or the like, can be repeatedly fastened, released, adjusted and then refastened. Acceptable embodiments of fasteners can include, for example and without limitation, adhesives, cohesives, mechanical fasteners such as buttons and corresponding buttonholes, snaps and the like, as well as other fasteners known to those skilled in the art which can be repeatedly fastened and released. Hook and loop fasteners are preferred because of their associated versatility and consumer acceptance.

Fastener-receptive area 18A can be constructed from a material which preferably has e.g. loop properties or hook material properties. In the alternative, any material which can form a cooperative relationship with desired fastener materials, such as those suggested above, to provide repeatable fastening and releasing properties, is suitable for use as, or in place of. fastener-receptive area 18A.

Still referring to personal care article 10A, the area of front portion 12A which is disposed between e.g. first line of weakness 30A and second line of weakness 32A defines a central section 46A of front portion 12A of the personal care article. Such line of weakness can comprise, for example, a line of breakable perforations or cuts. Lines of weakness are designed and constructed to be readily broken, but only if and when desired by a user or manufacturer. If desired, ones of the lines of weakness can be broken before the personal care article is placed around the torso of the wearer, in order to improve body fit by changing the size of the personal care article by use of one or both of fasteners 22 and 24 in combination with landing zone 18, as further described hereafter.

Again referring to personal care article 10A, a first lateral section 42A of front portion 12A is disposed between first line of weakness 30A and first side seam. 13A. A second lateral section 44A of front portion 12A is disposed between second line of weakness 32A and second side seam 15A. First and second lateral sections, 42A and 44A respectively, can be separated from and otherwise disassociated from central section 46A at respective lines of weakness 30A and 32A. Fasteners 22A, 24A function to enable the first and second lateral sections to be re-fastened onto fastener-receptive area 18A of central section 46A and subsequently released, multiple times. Thus, the wearer or an assistant or care giver can easily open and optionally adjust the personal care article, or remove the personal care article from the body of the wearer, and then refasten the personal care article on the wearer again, as desired.

The refastenable nature of the structures illustrated in the drawings also enables the user to release, adjust, and subsequently re-fasten the personal care article onto the body of the wearer. For example, if the personal care article is too loose upon putting the article as a pull-on pant, first and/or second lateral sections, 42A and 44A respectively, can be disassociated from central section 46A at respective lines of weakness 30A and 32A, whereupon respective fasteners 22A, 24A can be refastened to fastener-receptive area 18A at central section 46A. By moving fasteners 22A, 24A onto landing zone 18A, the user inherently reduces the size of the waist portion of the personal care article and thus obtains a tighter fit of the personal care article about the body of the wearer.

As used herein, "waist portion" means that portion of the respective personal care article which is disposed upwardly of first and second leg openings 31A, 33A, respectively (generically, leg openings 31, 33).

Preferred embodiments of FIGS. 1A, 1B, and 3 are illustrated and/or described as having landing zone material affixed to or integral with the outer cover of the respective absorbent article. Being cooperatively associated with the preferred location of the landing zone area, respective fasteners are preferably affixed to the interior portion, e.g. bodyside liner, of the respective absorbent article. While the preferred locations of the fasteners and landing zone are disclosed above, other embodiments are contemplated wherein the landing zone material is affixed to or integral with the bodyside liner, and the fasteners are affixed to the outer cover of the absorbent article.

Figure 2:
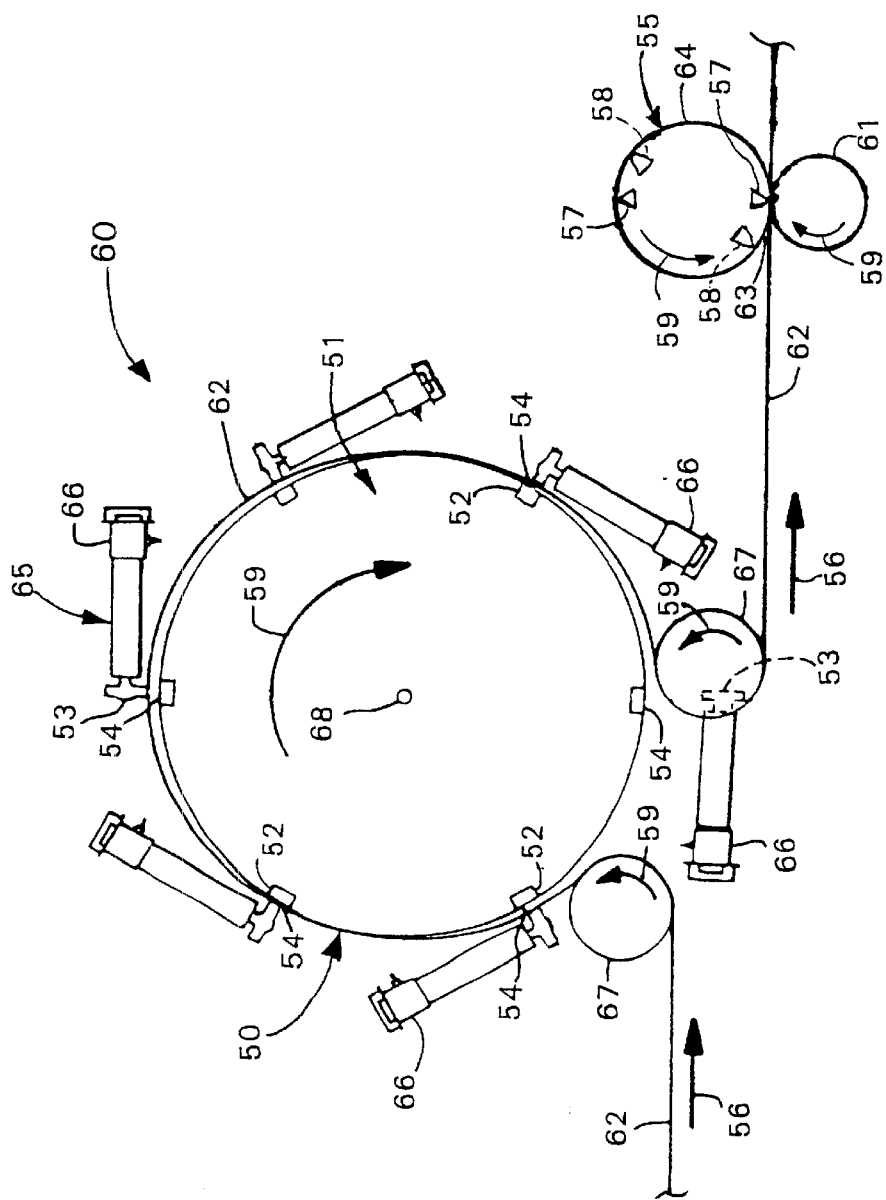
FIG. 2 shows a side elevation view of representative elements of a manufacturing line such as can be used in employing methods of the invention.

FIG. 2 representatively illustrates a portion of a manufacturing line 60 such as can be used in processes employing methods of the invention. Web 62, being a personal care article precursor, is drawn or fed through manufacturing line 60 using, among other means, e.g. turning rolls 67 to direct web 62 in the direction of manufacture indicated by arrow 56. Side seam bonder apparatus 50 is disposed along manufacturing line 60 and comprises multiple ultrasonic horn assemblies 65 and a working drum 51 which rotates about a central axis 68. Each horn assembly 65 comprises an ultrasonic horn 53 and a generator 66, and working drum 51 comprises multiple anvil components 52. U.S. Pat. No. 5,660,679 discloses a preferred embodiment of a side seam bonder apparatus of the invention. Thus, U.S. Pat. No. 5,660,679 is hereby incorporated by reference, in its entirety, into this application.

As web 62 is directed around the surface of working drum 51, respective segments of web 62 approach workstations 54 wherein respective ultrasonic horns 53 work in combination to form a nip with anvil components 52 of working drum 51 to effect side seams spaced by a first distance, e.g. the distance between 15A and 13B of FIG. 1A, in adjacent personal care article workpieces defined in the absorbent article precursor material of web 62 as such material passes through respective workstations 54.

Such side seams are preferably effected through the activation of ultrasonic-frequency energy in the horns. Less preferably, the side seams can also be effected through a variety of other means including thermal energy, application of adhesives, and other means known to those skilled in the art for forming side seam bonds in absorbent article precursors.

Still referring to FIG. 2, separation, e.g. cutter, apparatus 55 is disposed along manufacturing line 60 downstream side seam bonder apparatus 50. such that a respective portion of web 62 is affected by side seam bonder apparatus 50 prior to being affected by separation apparatus 55. Separation apparatus 55 comprises a cutter function roll 61 and final cutoff apparatus 64 having cutter components 57. Cutter components 57 are disposed at first positions on final cutoff apparatus 64 thereby to effect cuts/perforations in a cross-machine direction in at least portions of web 62 as web 62 passes through nip 63.

Separation apparatus 55 functions to cut and separate ones of the personal care articles from web 62 at e.g. line 17 of FIG. 1A to create stand-alone resultant personal care articles, ready for e.g. packaging or other suitable treatment. In the alternative, separation apparatus 55, via cutter components 57 working in combination with cutter function roll 61, can effect ones of perforation lines or other lines of weakness at e.g. line 17 of FIG. 1A in web 62, whereupon the personal care articles are separated from each other by subsequent tearing along the perforation lines or other lines of weakness.

Separation apparatus 55 is preferably a dual pitch knife cutting module, or the like. The dual pitch knife cutting module preferably has one knife operational, e.g. 57, for manufacture of personal care articles 10 (FIG. 1A) of the first relatively larger waist size wherein the one knife is employed to separate ones of the personal care articles of the first relatively larger size from the web at cut line 17, and two operational knives, e.g. 57. 58, for manufacture of personal care articles 11 (FIG. 1B) of the second relatively smaller waist size wherein the two knives 57, 58 are employed to separate ones of the personal care articles of the second relatively smaller size from the web at edges 26, 28 of excision section 25. While a dual pitch knife cutting module is preferred, some embodiments of the invention contemplate other cutting means known to those skilled in the art.

Preferably, to change sizing of the personal care articles produced using manufacturing line 60 from that of the first larger size shown in FIG. 1A to that of the second smaller size shown in FIG. 1B, anvil components 52 of a first size are interchanged with anvil components of a second size in side seam bonder apparatus 50. Similarly, ultrasonic horns 53 are changed out and replaced by horns of a second size to cooperatively act with respective anvil components 52 thereby increasing bond area of each respective workstation 54, such that the effective inactivated portion of the web indicated as cut zone 23, located between second side seam 15A and first side seam 13A of adjacent personal care articles 11A, 11B (respectively) of FIG. 1B, increases with respect to the inactivated portion of the web indicated as cut zone 23 in FIG. 1A.

Further, separation apparatus 55 is preferably modified by adding additional e.g. knives, illustrated in dashed outline as cutter components 58, such that the effective inactivated portion of the web indicated as cut zone 23, located between second side seam 15A and first side seam 13A of adjacent personal care articles 11A, 11B (respectively) of FIG. 1B, is cut along first and second edges 26, 28 of excision section 25 thus separating excision section 25 from web 62 wherein such excision section can be discarded.

Alternatively, size change can be accomplished by repositioning a side seam bonder apparatus along a manufacturing line, effecting other componential modifications to a side seam bonder apparatus, and/or re-programming a bonder apparatus to thereby adjust the timing, such that the effective inactivated portion of the web indicated as cut zone 23, located between second side seam 15A and first side seam 13A of adjacent personal care articles 11A, 11B (respectively) of FIG. 1B, increases with respect to the inactivated portion of the web indicated as cut zone 23 in FIG. 1A.

In such alternative methods for size change, separation apparatus 55 can also be relocated along manufacturing line 60, alternatively componentially modified, and/or re-programmed to adjust timing, such that excision section 25. comprising a significant portion of the effective inactivated portion of the web indicated as cut zone 23 disposed between second side seam 15A and first side seam 13A of adjacent personal care articles 11A, 11B (respectively) of FIG. 1B, can be separated along first and second side edges 26, 28 of excision section 25 and discarded, thus creating personal care articles exhibiting second different waist sizes, but substantially the same locations of positions of respective fasteners, landing zones, and lines of weakness as the first larger waist size personal care articles.

Methods of production resulting in size changes in personal care article precursors as related to lines 17, 26, 28, and side seam bonds 13, 15, can be accomplished by program changes to e.g. a programmable logic computer (not shown) which controls some or all of manufacturing line 60. An exemplary such computer is a PLC-5/80 Programmable Controller available from Rockwell Automation, Milwaukee, Wis., 53204-2496.

Such computer can function to implement desired timing and/or other programming changes to effect size changes, and/or physical adjustments along the manufacturing line, to manufacturing line components, such as, but not limited to, a feed roll servo motor, side seam bonder apparatus, cutting apparatus, and/or mechanical phasing. Relocation of positioning of side seams is made by e.g. re-timing the existing side seam bonder apparatus, thereby adjusting mechanical phasing.

Methods of the invention accomplish waist circumference size changes between a relatively smaller personal care article and a relatively larger personal care article by changing waist circumference. Waist circumference can be changed as follows. First, the user can break the lines of weakness 30A, 32A (e.g. FIG. 1A) and move the fasteners, e.g. 22A, 24A, onto the landing zone. Second, the manufacturer can change the location at which side seams are placed on the workpiece during assembly, as seen in a comparison of locations of the side seams, e.g. 13A, 15A, in FIGS. 1A and 1B, recognizing that the leading edge-to-leading edge distance "D1" is the same in both FIGS. 1A and 1B. Such change in location of placement of the side seams, in the machine direction, can be accomplished preferably by changing out components 52 of side seam bonder 50, by reprogramming or repositioning a side seam bonder, and/or by adjusting timing of a side seam bonder, wherein machine direction is substantially aligned with the direction of manufacture indicated by arrow 56 of FIG. 2. As a result of changing location of placement of the side seams during article manufacture, a larger inactivated effective length of waste material, indicated by excision section 25, is created between each respective active portion of web material of adjacent personal care article precursors on the manufacturing line, e.g. 10A, 10B.

"Machine direction", as applied herein, shall be understood to be synonymous to "with-machine direction".

In some embodiments, the method comprises, with respect to each workpiece, defining in the web or workpiece a length of material defined in the machine direction wherein activity of such length of material, in combination with other elements of the web or workpiece, determines the size of the article being produced, whereby the length of material can be activated to thereby produce relatively larger articles, or inactivated to produce relatively smaller articles. The method also comprises changing activity of the lengths of material so defined, thereby to affect size change in the respective articles being produced while maintaining the so-defined lengths of material in the web at least until the respective workpieces are separated from the web. In such embodiments, material is "activated" when such material is effectively used in the article to affect the size of the article. Extra and/or waste material, as well as portions of the respective article which are in the web or article, which could be used as part of the waist of the article but which are extraneous to the size of the article, define "inactivated" material. Material portions of a respective article or article precursor may be activated or inactivated by one or both of the manufacturer and the user.

An important feature of the method is that the article size, effectively the waist size of the personal care article, is changed while the repeat length of the workpieces, leading edge-to-leading edge, remains constant. With repeat length held constant, all assembly steps which are timed according to repeat length can be retained unchanged during such size change; and the only changes that need to be made are those pertaining to side seam bonds 13, 15 and the respective separation lines 17, 26, 28.

Referring to personal care article 10A of FIG. 1A, and article 11A of FIG. 1B as examples, location for placement of first side seam 13A and second side seam 15A are moved from the respective positions shown in FIG. 1A, inwardly on one or both of lateral sections 42A and 42B to the respective positions shown in FIG. 1B while retaining the positionings of lines of weakness 30A, 32A, fastener-receptive area 18A, and fasteners 22A, 24A to effect the change in the size of the wearer which the personal care article so manufactured will fit. Such change in the manufactured size can be implemented simply by changing timing and/or positioning of creation of side seams 13A, 15A. In the alternative, such change can be implemented by changing side seam bonder components, as suggested by the discussion of FIG. 2. As desired, the size change can be implemented by one or both of timing changes and component changes related to the side seam bonder apparatus.

Given the changed side seam placement shown in FIG. 1B, and the increased distance between adjacent personal care articles indicated by cut zone 23, the material between side seam 15A and side seam 13B is effectively "inactivated" as far as determining size of the personal care article. By comparison, a significant portion of the same machine direction length of material forms part of the waist area or front portion of the personal care article in FIG. 1A, whereby such length of material is "activated" in the embodiments of FIG. 1A. Thus, activation and inactivation are defined in terms of whether the respective length of material can be removed without affecting the size of the personal care article.

Referring to FIG. 1B, wherein side seams 13A, 15A have been placed inwardly, toward landing zone 18A, of the positions illustrated in FIG. 1A, such personal care articles are smaller in size than the personal care articles of FIG. 1A, as pull-on pants. When personal care articles 10A and/or 11A of FIGS. 1A and/or 1B, respectively, are used as diaper-like articles, by tearing lines of weakness 30A, 32A and repositioning the fasteners 22A, 24A on landing zone 18A, fasteners 22A, 24A can move a short distance to the edge of the landing zone, or as far as to where fasteners 22A, 24A are substantially abutting, or even overlapping, one another at or near a center portion of fastener-receptive area 18A.

The net effect of the changed position of side seams in FIG. 1B is that the length of inactivated material, referred to as excision section 25 of cut zone 23 between e.g. second side seam 15A and first side seam 13B can be removed without changing the size of article 11A. Since the side seam locations and resultant cut locations are the only portions of personal care article of the invention which change with manufacturing size changes, minimal on-line waste is generated in the process when compared to the amount of down-time avoided.

In summary, change in waist size of personal care articles of the invention can be achieved by e.g. a user tearing one or both of lines of weakness 30, 32 in combination with engaging one or both of fasteners 22, 24, respectively, with landing zone 18. Change in waist size of personal care articles of the invention can also be achieved by the manufacturer changing positions of side seams 13, 15 wherein repeat length of the workpieces, leading edge-to-leading edge, remains substantially constant while waist size of the articles is changed. Although the invention is directed to the latter method of waste size change wherein the repeat length of the workpieces remains constant, the former method employing use of the lines of weakness in combination with the fasteners and landing zone can be used in combination with the latter method wherein size changes of the invention are separately and independently implemented by the manufacturer.

Personal care articles of the invention can be used in at least two different ways. First, ones of personal care articles 10A of FIG. 1A and 11A of FIG. 1B, as shipped to the customer, can be used as pant-type structures. In such format, first and second lateral sections 42A and 44A are, and remain, attached separately to central section 46A at lines of weakness 30A and 32A, respectively. The pant-type structure is slipped onto the wearer while retaining attachment of first and second lateral sections 42A and 44A to central section 46A of the respective personal care article through lines of weakness 30A and 32A.

Accordingly, the legs of the wearer are inserted through the waist opening, and through the leg openings. The pant is then pulled upwardly until the leg openings are snugly positioned at the groin of the wearer. The wearer or caregiver can adjust the fitting of the pant-type structure to create a better relative positioning of the waist portion of the respective personal care article about the torso of the wearer, directed toward comfort of the wearer, thus to improve the fit.

So long as the article is used as a pant-type article, without separating the lateral sections from the central section as at lines of weakness 30A, 32A, the user's implementation of size control is in selection of the proper product size, as manufactured by the manufacturer. Further adjusting to obtain a tighter fit can be accomplished by the user by subsequent grasping and pulling of first and/or second lateral sections 42A and 44A, away from central section 46A along lines of weakness 30A and 32A, respectively, thereby to release first and/or second lateral sections 42A and 44A from central section 46A. Respective fasteners 22A and/or 24A, of first and/or second lateral sections 42A and 44A are then moved over fastener-receptive area 18A and fastened to fastener-receptive area 18A of central section 46A, so as to achieve the desired relationship between adjusted size of the respective personal care article and size of the wearer. Release and refastening of fasteners 22A and 24A can occur multiple times (e.g. an indeterminate number of times) to enable proper fitting throughout the expected use life of the personal care article. Fasteners 22A and 24A of first and second lateral sections 42A and 44A, respectively, can be adjusted individually or in combination with each other to create a relatively tighter or relatively looser fit, though all such fits are tighter than the fit of the pant-type articles shown in FIGS. 1A and 1B, wherein neither of the lines of weakness 30A. 32A have been broken.

The second method of using ones of personal care articles 10A of FIG. 1A and 11A of FIG. 1B is to use ones of such articles as a diaper-like article. In use as a diaper-like article and before putting such article on the prospective wearer, first and second lateral sections 42A and 44A are separated from central section 46A of the personal care article at lines of weakness 30A and 32A, and front portion 12A is pulled away from back portion 16A. In the method of using such article as a diaper-like article, the separation of first and second lateral sections 42A and 44A from central section 46A can be performed before packaging by the manufacturer, or can be performed anytime prior to or during use by the user. After the lateral sections are separated from the central section, the personal care article is laid on a preferably horizontal surface with the bodyside liner facing upwardly. The lower portion of the torso of the wearer (e.g. infant or adult) is then laid or otherwise moved onto back portion 16A of the personal care article. Front portion 12A is then brought frontwardly between the legs of the wearer and onto the torso of the wearer. Lateral sections 42A and 44A are fastened, via first and second fasteners 22A and 24A, to fastener-receptive area 18A, completing the application of the personal care article onto the wearer. With possible exception of the separation of the lateral sections from the central section at the respective lines of weakness, those skilled in the art will recognize the instant above description as a known method of putting a diaper-like article on a wearer.

Alternative methods of putting on a diaper-like article will be obvious to those of ordinary skill in the art. Such alternative methods include, but are not limited to, e.g. putting the diaper-like article on a wearer when such wearer is in a position other than lying down, e.g. standing, and/or when such wearer's slacks/pants are not entirely removed, but rather, lowered to expose the lower trunk and groin region of the wearer.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. In a process for manufacturing pant-type refastenable personal care articles in a format which includes defining a stream of workpieces connected to each other along a web having an indefinite length, a respective such personal care article having a front portion, a rear portion, and a crotch portion, a method of changing from manufacture of such pant-type refastenable personal care articles of a first size to manufacture of such pant-type refastenable personal care articles of a second different size, the method comprising, (a) with respect to such workpieces, defining in the respective web or workpiece a length of material defined in a machine direction wherein activity of such length of material, in combination with other elements of the web or workpiece, determines the size of the pant-type refastenable personal care article being so produced, whereby the length of material can be activated to thereby produce relatively larger such personal care articles, or inactivated to produce relatively smaller personal care articles; and (b) changing activity of at least one of the lengths of material so defined, thereby to effect size change in the respective personal care articles being produced while maintaining the so-defined lengths of material in the web at least until the respective workplaces are separated from the web.

2. A method as in claim 1, such workpieces, including the defined length of material, having a common dimension, leading edge-to-leading edge, in the machine direction of such manufacturing process both with inclusion of the length of material and with exclusion of the length of material.

3. A method as in claim 1 wherein first and second side seam bonds are formed on opposing sides of respective ones of adjoining workpieces, and wherein inboard edges of adjacent side seam bonds on adjacent workpieces are spaced from each other by a first distance, the method further including changing the activity of the length of material by manufacturing workpieces having the inboard edges of adjacent such side seam bonds spaced from each other by a second distance different from the first distance.

4. A method as in claim 1 wherein first and second side seam bonds are formed on opposing sides of respective ones of adjoining workpieces, and wherein inboard edges of adjacent side seam bonds on adjacent workpieces are spaced from each other by a first distance, the method further including inactivating the length of material by manufacturing workpieces having the inboard edges of adjacent such side seam bonds spaced from each other by a second distance greater than the first distance.

5. A method as in claim 1, including changing one or both timing and loci of side seam bonder apparatus components, and thus location of forming of side seam bonds on the respective workpieces, in combination with one or both timing and loci of separation apparatus components, and thus location of formation of cuts separating such workpieces from the web, and thereby effecting a size change in the personal care articles being so produced, sufficient in magnitude to be discernable in routine consumer distribution.

6. In a process for manufacturing pant-type refastenable personal care articles in a format which includes defining a stream of workpieces connected to each other along a web having an indefinite length, a respective such personal care article having a front portion, a rear portion, and a crotch portion, respective ones of the workpieces being joined to each other at respective side edges of such workpieces, a method of changing from manufacture of such pant-type refastenable personal care articles of a first size to manufacture of such pant-type refastenable personal care articles of a second different size, the method comprising, (a) with respect to such workpieces, defining in the respective web or workpiece, at at least one side edge of the respective workpiece, a length of material defined in a machine direction, wherein activity of such length of material, in combination with other elements of the web or workpiece, determines the size of the pant-type refastenable personal care article being so produced, whereby the length of material so defined can be activated and thereby incorporated into the personal care article to correspondingly produce a relatively larger such personal care article, or inactivated and thereby excluded from the personal care article to correspondingly produce a relatively smaller personal care article;

(b) changing activity of at least ones of the lengths of material so defined, thereby to effect size change in the respective personal care articles being produced while maintaining the so-defined lengths of material in the web at least until the respective workpieces are separated from the web.

7. A method as in claim 6, such workpieces, including the defined length of material, having a common dimension, leading edge-to-leading edge, in the machine direction of such manufacturing process both with inclusion of the length of material and with exclusion of the length of material.

8. A method as in claim 6, including defining first and second such lengths of material at opposing first and second such side edges of the respective workpiece, and controlling activity of such lengths of material thereby to determine the size of the respective pant-type refastenable personal care article.

9. A method as in claim 6 wherein first and second side seam bonds are formed on opposing sides of respective ones of adjoining workpieces, and wherein inboard edges of adjacent side seam bonds on adjacent workpieces are spaced from each other by a first distance, the method further including changing the activity of the length of material by manufacturing workpieces having the inboard edges of adjacent such side seam bonds spaced from each other by a second distance different from the first distance.

10. A method as in claim 6 wherein first and second side seam bonds are formed on opposing sides of respective ones of adjoining workpieces, and wherein inboard edges of adjacent side seam bonds on adjacent workpieces are spaced from each other by a first distance, the method further including inactivating the length of material by manufacturing workpieces having the inboard edges of adjacent such side seam bonds spaced from each other by a second distance greater than the first distance.

11. A method as in claim 6, including changing one or both timing and loci of side seam bonding apparatus components, and thus location of forming of side seam bonds on the respective workpieces from the web, and thereby effecting a size change in the personal care articles being so produced, sufficient in magnitude to be discernable in routine consumer distribution.

12. In a process for manufacturing pant-type refastenable personal care articles in a format which includes defining a stream of workpieces connected to each other along a web having an indefinite length, a respective such personal care article having a front portion, a rear portion, and a crotch portion, respective ones of the workpieces being joined to each other at respective side edges of such workpieces, each such workpiece having bonds joining the front portion and the rear portion to each other at the side edges, each such bond having an inwardly-disposed edge disposed away from the respective side edge of such workpiece, a method of changing from manufacture of such pant-type refastenable personal care articles of a first size to manufacture of such pant-type refastenable personal care articles of a second different size, the method comprising, (a) with respect to each workpiece, defining in the web or workpiece, at the side edges of the respective workpiece, a length of material defined in a machine direction, wherein incorporation of such length of material, in combination with other elements of the web or workpiece, inwardly of the inwardly-disposed edges, produces a pant-type refastenable personal care article of a relatively larger size, and wherein exclusion of such length of material from the workpiece produces a pant-type refastenable personal care article of a relatively smaller size; and (b) changing use of the lengths of material so defined, from inclusion to exclusion or from exclusion to inclusion, thereby to effect size change in the respective personal care articles being produced while maintaining the so-defined lengths of material in the web at least until the respective workpieces are separated from the web.

13. A method as in claim 12, such workpieces, including the defined length of material, having a common dimension, leading edge-to-leading edge, in the machine direction of such manufacturing process both with inclusion of the length of material and with exclusion of the length of material.

14. In a process for manufacturing pant-type refastenable personal care articles in a format which includes defining a stream of workpieces connected to each other along a web having an indefinite length, a respective such personal care article having a front portion, a rear portion, and a crotch portion, a method of changing from manufacture of such pant-type refastenable personal care articles of a first size to manufacture of such pant-type refastenable personal care articles of a second different size, the method comprising, (a) with respect to such workpieces, defining in the respective web or workpiece a length of material defined in a machine direction wherein activity of such length of material, in combination with other elements of the web or workpiece, determines the size of the pant-type refastenable personal care article being so produced, whereby the length of material can be activated to thereby produce relatively larger such personal care articles, or inactivated to produce relatively smaller personal care articles;

(b) initiating a such manufacturing process and thereby beginning manufacture of an ongoing stream of such personal care articles; and (c) while continuing to manufacture the ongoing stream of such personal care articles, changing activity of part or all of ones of the lengths of material so defined, thereby to effect a size change in the respective personal care articles being produced.

15. A method as in claim 14 wherein first and second side seam bonds are formed on opposing sides of respective ones of adjoining workpieces, and wherein inboard edges of adjacent side seam bonds on adjacent workpieces are spaced from each other by a first distance, the method further including changing the activity of the length of material by manufacturing workpieces having the inboard edges of adjacent such side seam bonds spaced from each other by a second distance different from the first distance.

16. A method as in claim 14 wherein first and second side seam bonds are formed on opposing sides of respective ones of adjoining workpieces, and wherein inboard edges of adjacent side seam bonds on adjacent workpieces are spaced from each other by a first distance, the method further including inactivating the length of material by manufacturing workplaces having the inboard edges of adjacent such side seam bonds spaced from each other by a second distance greater than the first distance.

17. A method as in claim 14 including separating successive ones of the workpieces from the web, and including separating the inactivated lengths of material from both of the adjacent respective workpieces.

18. A method as in claim 14 including changing one or both timing and loci of side seam bonding apparatus components, and thus location of forming of side seam bonds on the respective workpieces, in combination with one or both timing and loci of separation apparatus components, and thus location of formation of cuts separating such workpieces from the web, and thereby effecting a size change in the personal care articles being so produced, sufficient in magnitude to be discernable in routine consumer distribution.

19. A method as in claim 18, including employing a programmable logic computer (i) to instruct side seam bonding apparatus regarding one or both proper timing and positioning of side seam bonding apparatus components, and thus location for forming the side seam bonds, and (ii) to instruct separation apparatus regarding one or both proper timing and positioning of separation apparatus components, and thus location on the workpieces for separation of the respective workpieces from the web, and from the inactivated lengths of material.

* * * * *

UNITED STATES PATENT AND TRADEMARK OFFICE
CERTIFICATE OF CORRECTION

PATENT NO. : 6,454,888 B1
DATED : September 24, 2002
INVENTOR(S) : Denise Marie Bell Murie et al.

It is certified that error appears in the above-identified patent and that said Letters Patent is hereby corrected as shown below:

Title page,
Item [76], Inventors, add -- Suzanne Marie Schmoker, 4212 Brooks Road, Oshkosh, WI 54904 -- as the fifth and final inventor.
Add Item:
-- [73] Assignee: Kimberley-Clark Worldwide, Inc., Neenah, Wis. --

Signed and Sealed this

Sixteenth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,454,888 B1
DATED : September 24, 2002
INVENTOR(S) : Denise Marie Bell Murie et al.

It is certified that error appears in the above-identified patent and that said Letters Patent is hereby corrected as shown below:

Title page,
Item [76], Inventors, add -- Suzanne Marie Schmoker, 4212 Brooks Road, Oshkosh, WI 54904 -- as the fifth and final inventor.
Add Item:
-- [73] Assignee: Kimberly-Clark Worldwide, Inc., Neenah, Wis. --

This certificate supersedes Certificate of Correction issued November 16, 2004.

Signed and Sealed this

Twenty-third Day of August, 2005

JON W. DUDAS
*Director of the United States Patent and Trademark Office*